United States Patent
Kajino et al.

(10) Patent No.: US 8,134,710 B2
(45) Date of Patent: Mar. 13, 2012

(54) PARTICULATE DETECTOR SYSTEM

(75) Inventors: Keiichi Kajino, Tokyo (JP); Mitsuharu Iwasaki, Kanagawa-ken (JP); Tatsuyuki Nihei, Tokyo (JP)

(73) Assignee: Texas Instruments Incorporated, Dallas, TX (US)

( * ) Notice: Subject to any disclaimer, the term of this patent is extended or adjusted under 35 U.S.C. 154(b) by 107 days.

(21) Appl. No.: 12/791,426

(22) Filed: Jun. 1, 2010

(65) Prior Publication Data

US 2010/0302545 A1    Dec. 2, 2010

(30) Foreign Application Priority Data

Jun. 1, 2009 (JP) ................... 2009-132364

(51) Int. Cl.
*G01N 21/17* (2006.01)
*G01N 21/53* (2006.01)
*G08B 17/10* (2006.01)

(52) U.S. Cl. ........ 356/436; 356/338; 356/336; 340/630; 340/691.6

(58) Field of Classification Search .......... 356/432–444, 356/336–342; 250/574, 575; 430/630, 628, 430/691.6, 691.8
See application file for complete search history.

(56) References Cited

U.S. PATENT DOCUMENTS

| 4,412,323 | A  | * | 10/1983 | Abbott et al. | 370/217 |
| 5,936,986 | A  | * | 8/1999  | Cantatore et al. | 372/38.02 |
| 7,167,099 | B2 | * | 1/2007  | Kadwell et al. | 340/630 |
| 7,457,709 | B2 | * | 11/2008 | Zhang et al. | 702/26 |
| 7,788,969 | B2 | * | 9/2010  | Verdegan | 73/61.69 |

OTHER PUBLICATIONS

"Cyber Sensor," Matsushita Electric Works Technical Report, Matsushita Electric Works, Ltd., Feb. 2003, No. 80, pp. 75-83, (Report).

* cited by examiner

*Primary Examiner* — Sang Nguyen
(74) *Attorney, Agent, or Firm* — John J. Patti; Wade J. Brady, III; Frederick J. Telecky, Jr.

(57) ABSTRACT

A particulate detector system is provided that can sense particulates (such as smoke in the air). The system employs a reflected light system that generally avoids making measurements of light intensity. Instead, coded signals are compared with one another to determine error rates between emitted light and detected light (across a chamber). Based on the error rate, processing circuitry can determine particulate concentration.

20 Claims, 5 Drawing Sheets

PARTICULATE DETECTOR SYSTEM

CROSS-REFERENCE TO RELATED APPLICATIONS

This application is claims priority from Japanese Patent Application No. 2009-132364, filed Jun. 1, 2009, which is hereby incorporated by reference for all purposes.

TECHNICAL FIELD

The invention relates generally to a sensor and, more particularly, to a particulate sensor or detector that senses particulates (such as smoke and dirt) in the air.

BACKGROUND

A conventional commercial use of a particulate sensor is a smoke detector, and an example description for such a sensor can be found in Nishikawa et al., "Cyber Sensor," *Matsushita Electric Works Technical Report, Matsushita Electric Works, Ltd.*, February 2003, No. 80, pp. 75-83 ("Report"). In the Report, a smoke detector senses smoke by utilizing scattered infrared light, where an emitter and a detector are installed in a chamber surrounded with a reflecting plate (called a labyrinth). The labyrinth has a structure in which smoke can flow in (from outside) so that smoke can block the infrared from reaching the detector. In other words, the smoke is sensed by the change in the quantity of light received by detector.

In order to determine the concentration of smoke based on a slight quantity of received light, it is generally necessary to amplify analog signals that are output from the detector using a low-noise and high-gain amplifier. Additionally, an analog-to-digital converter (ADC) is also used to enable further digital processing. Therefore, in the conventional smoke sensor, the scale of the circuit is enlarged due to the high-gain amplifier the ADC, and there is a need for smaller circuits.

SUMMARY

In accordance with a preferred embodiment of the present invention, an apparatus is provided. The apparatus comprises a signal generator that receives a clock signal; a driver that is coupled to the signal generator; an emitter that is coupled to the driver, wherein the emitter emits light; a detector that is adapted to receive light emitted from the emitter; a signal regenerator that receive the clock signal and that is coupled to the detector; an error detector that is coupled to the signal regenerator and to the signal generator, wherein the error detector compares a set of bits output from the signal generator to a corresponding set of bits output from the signal regenerator and determines the number of errors between the sets of bits output from the signal generator and the signal regenerator; and processing circuitry that is coupled to the error detector so as to compare the number of error to a threshold to determine a particulate concentration between the emitter and the detector.

In accordance with a preferred embodiment of the present invention, the apparatus further comprises an amplifier that is coupled between the detector and the signal regenerator.

In accordance with a preferred embodiment of the present invention, the apparatus further comprises a clock generator that is coupled to the signal generator and the signal regenerator.

In accordance with a preferred embodiment of the present invention, the apparatus further comprises an intensity adjustment circuit that is coupled to the error detector and the driver, wherein the intensity adjustment circuit adjusts a drive current for the emitter.

In accordance with a preferred embodiment of the present invention, the apparatus further comprises a pulse width modulator (PWM) that is coupled to the error detector and the driver, wherein the intensity adjustment circuit adjust the pulse width of a drive signal for the emitter.

In accordance with a preferred embodiment of the present invention, the apparatus further comprises a bit length adjustment circuit that is coupled to the error detector.

In accordance with a preferred embodiment of the present invention, the bit length adjustment circuit is coupled to the signal generator.

In accordance with a preferred embodiment of the present invention, the apparatus further comprises a bit rate adjustment circuit that is coupled to the error detector and the signal generator.

In accordance with a preferred embodiment of the present invention, the apparatus further comprises: an average value calculator that is coupled to the error detector; and a threshold adjustment circuit that is coupled to the average value calculator and the processing circuitry.

In accordance with a preferred embodiment of the present invention, the apparatus further comprises: a carrier signal generator; a modulator that is coupled to carrier signal generator and that is coupled between the signal generator and the driver; and a demodulator that is coupled to the clock generator and the carrier signal generator and that is coupled between the amplifier and the error detector.

In accordance with a preferred embodiment of the present invention, an apparatus is provided. The apparatus comprises a chamber; a signal generator that receives a clock signal; a driver that is coupled to the signal generator; an emitter that is coupled to the driver and that is secured to the chamber, wherein the emitter emits light; a detector that is adapted to receive light emitted from the emitter and that is secured to the chamber; a signal regenerator that receive the clock signal and that is coupled to the detector; an error detector that is coupled to the signal regenerator and to the signal generator, wherein the error detector compares a set of bits output from the signal generator to a corresponding set of bits output from the signal regenerator and determines the number of errors between the sets of bits output from the signal generator and the signal regenerator; and processing circuitry that is coupled to the error detector so as to compare the number of error to a threshold to determine a particulate concentration within the chamber between the emitter and the detector.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1:
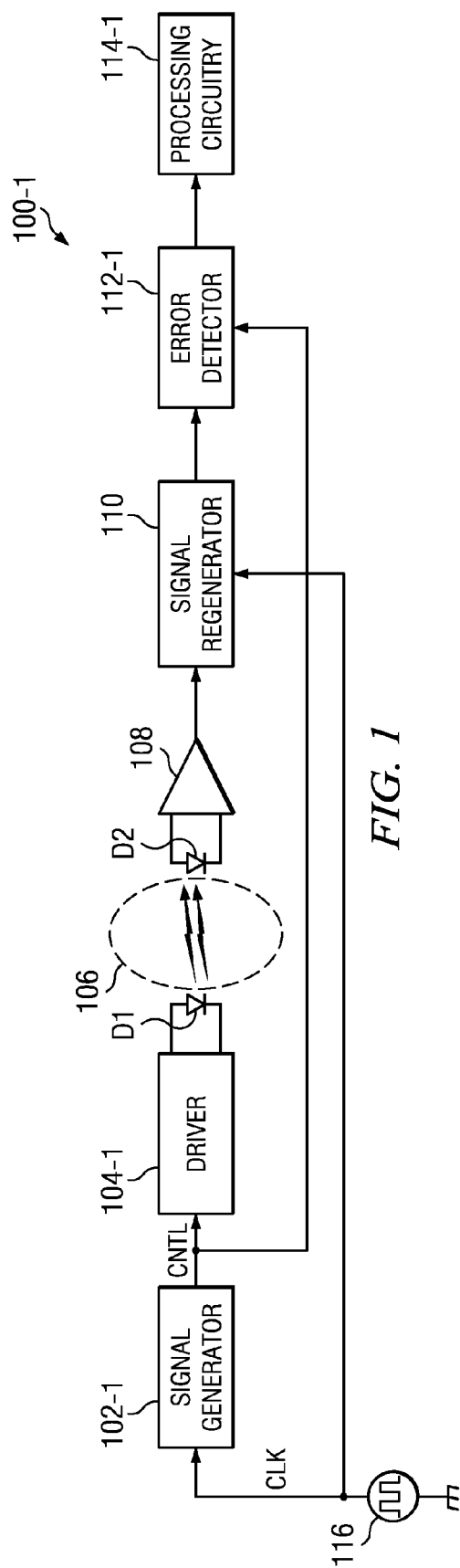
FIGS. 1 and 3-9 are block diagrams of examples of particulate detector systems in accordance with a preferred embodiment of the present invention.

Refer now to the drawings wherein depicted elements are, for the sake of clarity, not necessarily shown to scale and wherein like or similar elements are designated by the same reference numeral through the several views.

Figure 2:
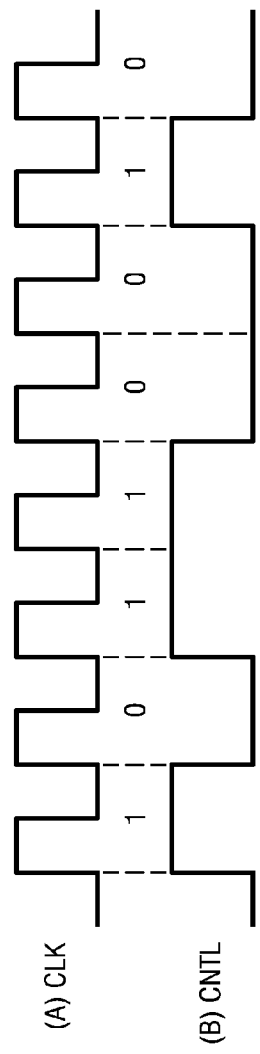
FIG. 2 is a timing diagram depicting an example of a clock signal and a control signal for the system of FIG. 1.

Turning to FIGS. 1 and 2, an example of a particulate detector system 100-1 can be seen. System 100-1 generally comprises a clock generator 116, a signal generator 102-1, a driver 104-1, an emitter D1, a chamber 106, a detector D2, an amplifier 108, signal regenerator 110, a error detector 112-1, and processing circuitry 114-1. In operation, the signal generator generates a control signal CNTL based at least in part on the clock signal CLK from clock generator 116. Typically, signal generator 102-1 repeatedly generates bit patterns (or pseudorandom noise codes) with a fixed bit length having a property reduce to random noise, which can be seen in FIG. 2. Based on this control signal CNTL, driver 104-1 drives the emitter D1 (which is generally a light-emitting diode or LED) so that light (typically infrared light) can propagate across chamber 106. The chamber 106 is generally an optical system in which particulates to be sensed may be present (for example, a labyrinth of a smoke detector). The detector D2 (which is typically a photodiode) receives light that traverse the chamber 106. each of the emitter D1 and detector D2 are also secured to the chamber 106. For example, a light-receiving surface of the optical system (which includes chamber 106) for light reception is arranged opposite to the light-emitting surface. Amplifier 108, then, amplifies the signal from the detector D2, and the signal regenerator 110 regenerates the pseudorandom noise codes from the amplified signal. As an example, the signal regenerator may comprise a comparator circuit and a latch circuit, where the comparator circuit compares the amplified signals with a threshold to output a comparison result that is latched by the latch circuit latches. The error detector 112-1 then compares the control signal CNTL to the output from the signal regenerator 110 to determine if there is an error. For example, the error detector 112-1 compares a bit strings from the signal generator 102-1 and signal regenerator 110 over a predetermined detection bit length and counts the number of bits (error bits) with different values in the comparison so as to detect the number of bit errors per detection bit length. Based on the signal from the error detector 112-1, the processing circuitry 114-1 can compare the number of error bits per detection bit length with a predetermined threshold so as to determine the concentration of particulates in the chamber 106. For example, the processing circuitry 114-1 can output a decision signal showing whether the number of error bits exceeds the prescribed decision threshold or can compare the number of error bits with several decision thresholds and output a decision signal showing the particulate concentration corresponding to the range of the threshold to which the number of error bits belongs.

As explained above, in the system 100-1, if the concentration of particulates in chamber 106 rises, the light emitted by the emitter D1 is scattered, hindering the transmission of the light to the detector D2. When the transmission of the signals is hindered, the error rate (the number of error bits) detected by the error detector increases. Therefore, since the particulates are sensed in accordance with the error rate, it is not necessary to precisely measure the size of the signals of the scattered light, so there is no need for an ADC. Additionally, it is not necessary to amplify the light detecting signals with high gain, unlike a conventional device for sensing particulates based on a slight intensity change in scattered signals.

Figure 3:
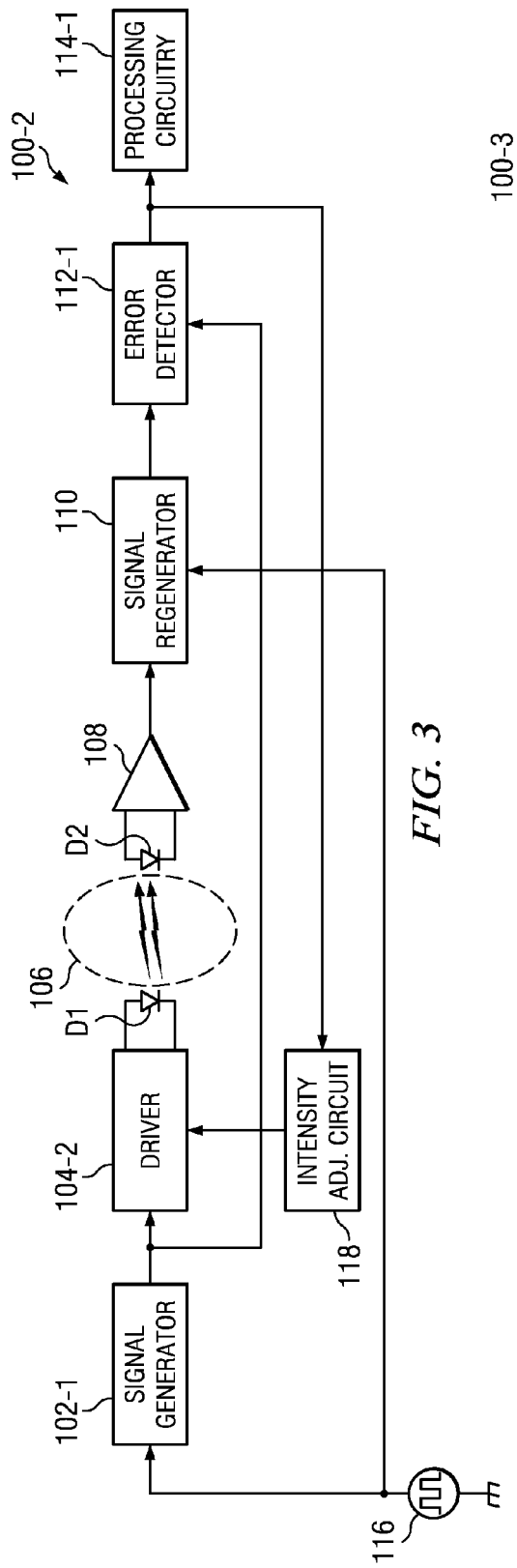

Turning now to FIG. 3, system 100-2 can be seen. System 100-2 has generally the same structure as system 100-1. However, driver 104-1 has been replaced with driver 104-2, and intensity adjustment circuit 118 has been included. The inclusion of the intensity adjustment circuit 118 allows system 100-2 to operate in two modes of operation: detection mode and adjustment mode. In the adjustment mode, circuit 118 provides a control signal to driver 104-2 to adjust the drive current for emitter D1, which may be accomplished by varying the output current of a current source or by selectively switching several current sources with different current values. A reason for performing this adjustment in the adjustment mode is to generally determine whether that the number of error bits counted by the error detector 112-1 is included in a predetermined range or (in other words) to calibrate system 100-2 in accordance with nominal particulate concentrations. For example, for a sufficiently low particulate concentration, the number of error bits is included in a prescribed lower limit range.

Figure 4:
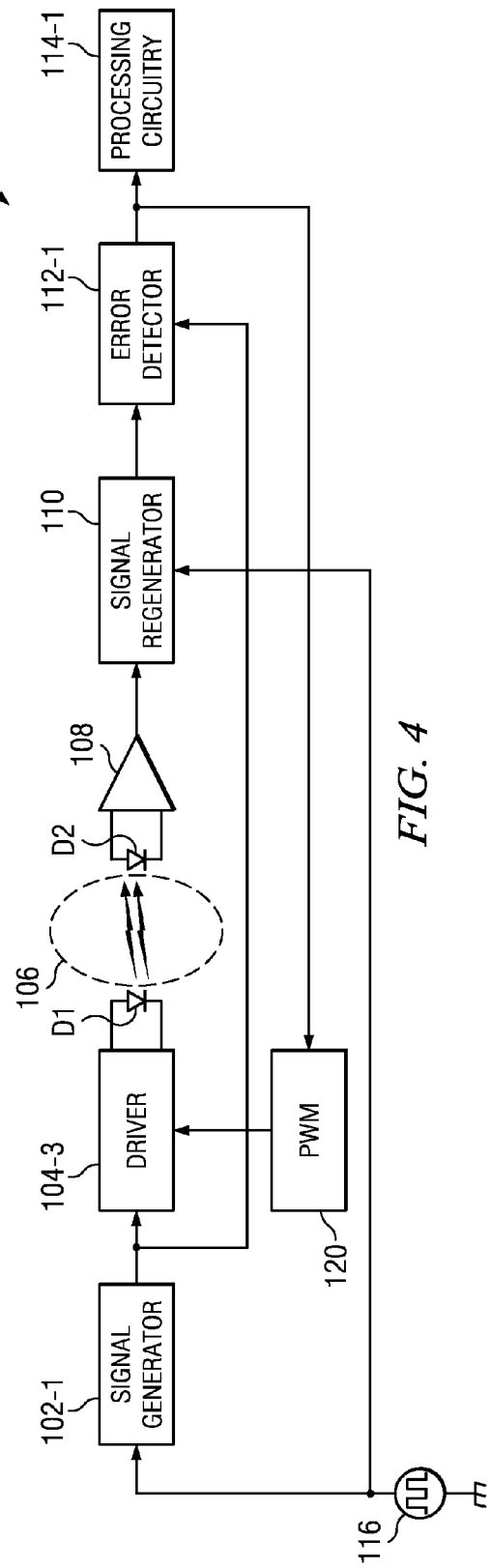

In FIG. 4, system 100-3 can be seen. System 100-3 has generally the same structure as system 100-1. However, driver 104-1 has been replaced with driver 104-3, and pulse width modulator or PWM 120 has been included. System 100-3 has similar functionality to system 100-2, in that the amplitude or intensity of the light emitted from emitter D1 can be adjusted. System 100-3, instead of adjusting a driver current, uses the PWM 120 to adjust the drive signal for the emitter D1.

Figure 5:
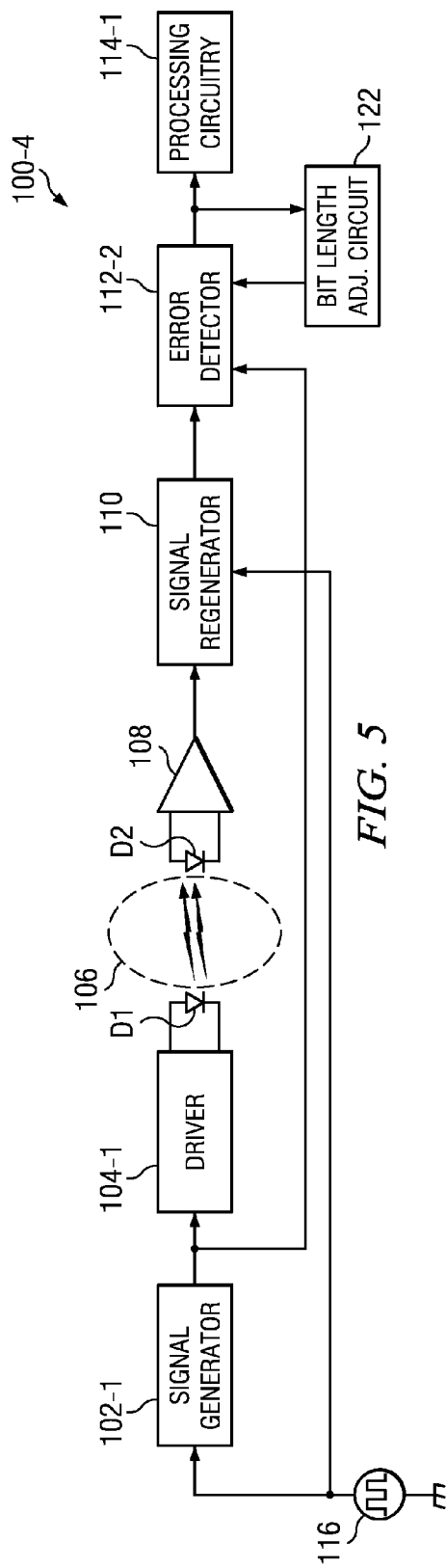

Turning now to FIG. 5, system 100-4 can be seen. System 100-4 has generally the same structure as system 100-1. However, error detector 112-1 has been replaced by error detector 112-2 and bit length adjustment circuit 122 has been included. Here, the detection range can be adjusted by changing the detection bit length when the number of error bits is counted. Preferably, bit length adjustment circuit 122 changes the detection bit length in an adjustment mode so that the ratio (bit error rate) of error bits to the detection bit length of the error detector 112-2 is within a predetermined range. Thus, if the bit length is lengthened, the detection range at the low concentration side is expanded.

Figure 6:
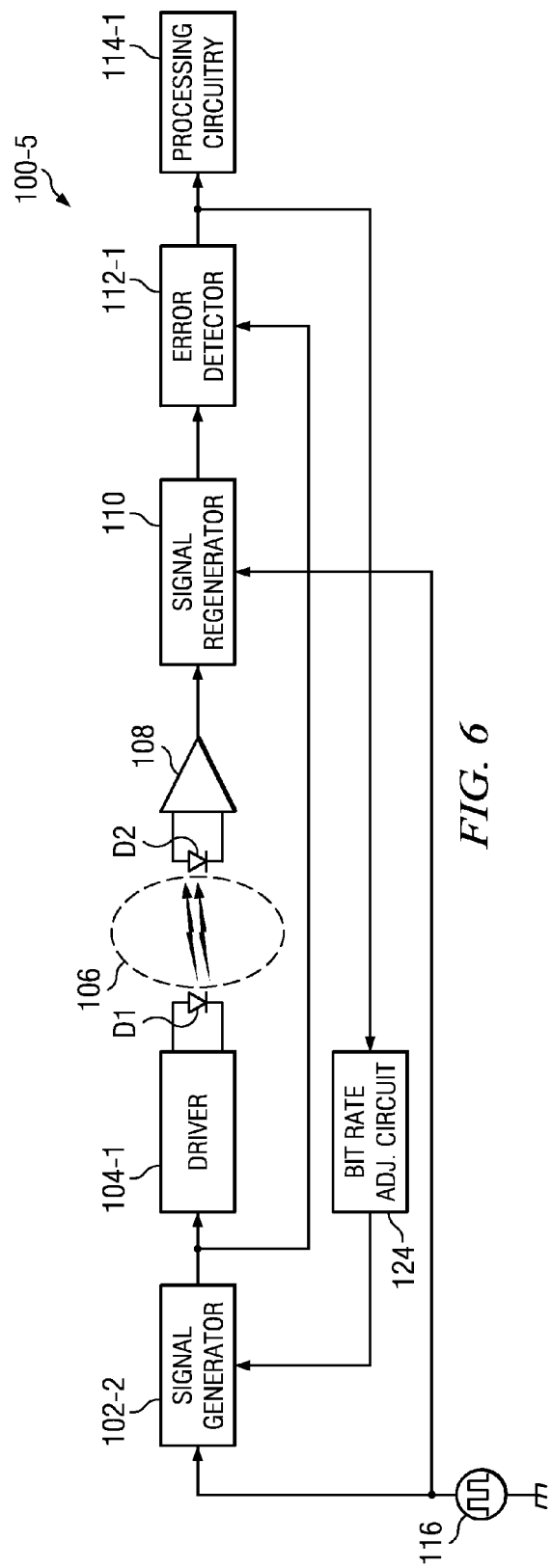

In FIG. 6, system 100-5 can be seen. System 100-5 has generally the same structure as system 100-1. However, signal generator 102-1 has been replaced with signal generator 102-2, and bit rate adjustment circuit 124 has been included. Typically, signal generator 102-2 includes a frequency synthesizer, and this frequency synthesizer can be adjusted by the bit rate adjustment circuit 124. The bit rate adjustment part 93 changes the bit rate of the PN codes in an adjustment mode so that the number of error bits of the error detection part 60 is included in a predetermined range. Preferably, if the bit rate of the codes is changed, the frequency band of the codes is changed. In other words, the frequency band of the light signals is shifted to the high frequency side with an increase in the bit rate of the codes and shifted to the low frequency side with a decrease in the bit rate of the codes. Therefore, for example, even if the number of bit errors reaches an abnormal value due to an abrupt variation in a noise environment such as external noise, the number of error bits can be returned to a normal range by shifting the frequency band of the light signals. Thereby, a decrease in the detection precision due to external noise can be effectively suppressed.

Figure 7:
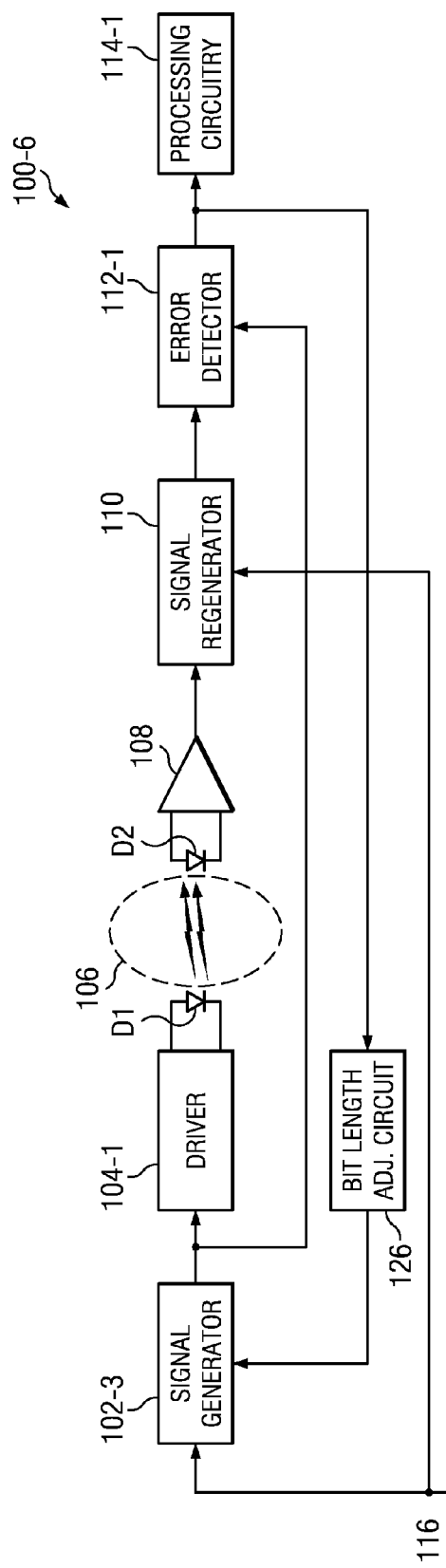

Turning to FIG. 7, system 100-6 can be seen. System 100-6 has generally the same structure as system 100-1. However, signal generator 102-1 has been replaced with signal generator 102-3, and bit length adjustment circuit 126 has been included. Here, the frequency band of light signals is adjusted by changing the bit patterns of codes for the signal generator 102-3, where bit length adjustment circuit 126 changes the bit length of the codes in an adjustment mode so that the number of error bits is included in a predetermined range. Preferably, if the bit length of the codes is changed, the bandwidth of the frequency band of the codes is changed. Thus, even if noise varies, the number of error bits can be returned to a normal range by changing the bandwidth of the light signals. Therefore, a decrease in the detection precision due to an external noise can be effectively suppressed.

Figure 8:
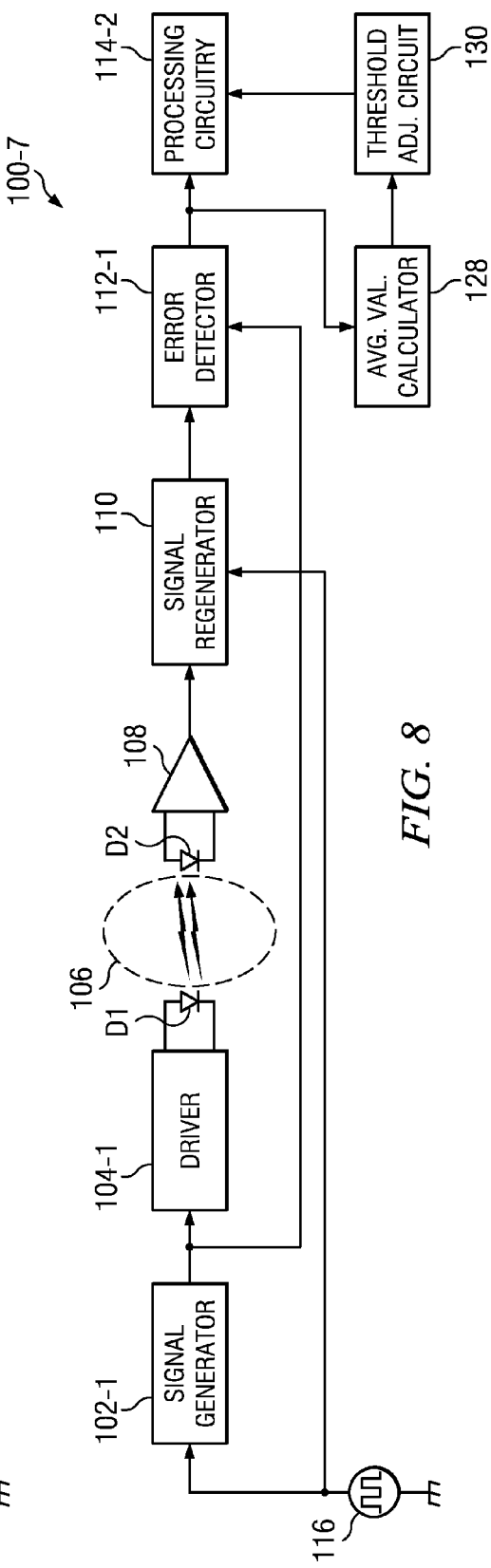

In FIG. 8, system 100-7 can be seen. System 100-7 has generally the same structure as system 100-1. However, processing circuitry 114-1 is replaced by processing circuitry 114-2, and average value calculator 128 and threshold adjustment circuit 130 are included. Here, a threshold for determining particulate concentration is varied. Preferably, average value calculator 128 calculates an average value of the number of error bits that are counted in the error detector 112-1, and the threshold for determining particulate concentration is varied accordingly by the threshold adjustment circuit. For example, the average value calculator 128 calculates a moving average of the number of error bits by integrating the counted results of a series of numbers of error bits at any time, and the decision threshold adjustment circuit 130 sets the decision threshold at a value in which a predetermined offset value is added to the average value of the number of error bits. Thus, even if the average value of the number of error bits in a normal state is changed by a peripheral environment (for example, brightness), since the threshold can be set in accordance with the change, a change in the particulate concentration from the normal state can be appropriately sensed.

Additionally, the frequency band of light signals is diffused by using pseudorandom noise codes, but alternatively, another encoding such as RZ (return to zero) and CMI (coded mark inversion signal) may also be applied to the pseudorandom noise codes.

Figure 9:
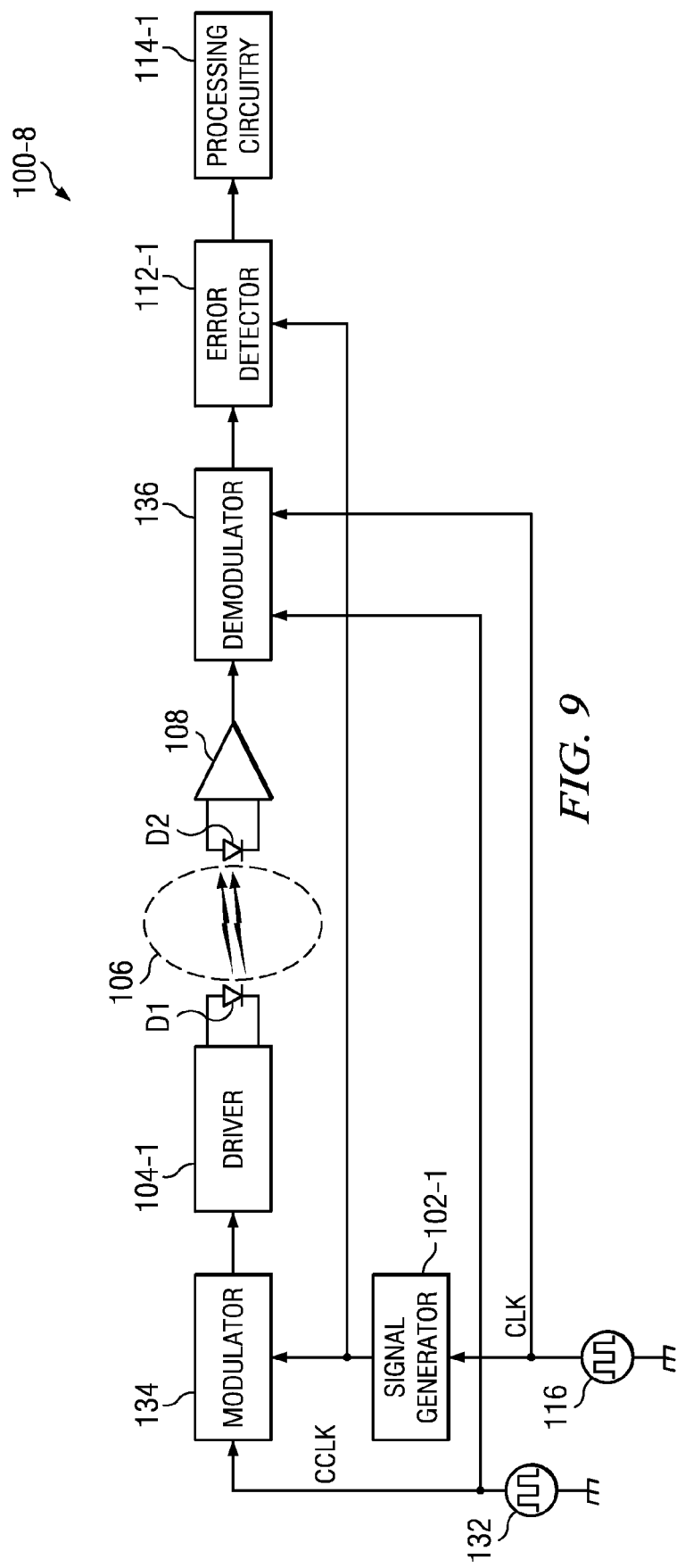

Turning to FIG. 9, system 100-8 can be seen. System 100-8 has generally the same structure as system 100-1. However, carrier signal generator 132, modulator 134, and demodulator 136 have been included. Here, a carrier signal CLK is generated by the carrier signal generator 132 (which is higher than the synchronized with the clock signal CLK). Modulator 134 can then modulate the carrier signal CCLK by pseudorandom noise codes. Additionally, demodulator 136 demodulates the codes based on the carrier signal CCLK. For example, demodulator 136 multiplies the output signal of the amplifier 108 by the carrier signal CCLK and demodulates the code component (synchronous detection) by removing the carrier signal CCLK from the signal after multiplication through a low-pass filter circuit.

Having thus described the invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the invention may be employed without a corresponding use of the other features. Accordingly, it is appropriate that the appended claims be construed broadly and in a manner consistent with the scope of the invention.

The invention claimed is:

1. An apparatus comprising:
   a signal generator that receives a clock signal;
   a driver that is coupled to the signal generator;
   an emitter that is coupled to the driver, wherein the emitter emits light;
   a detector that is adapted to receive light emitted from the emitter;
   a signal regenerator that receive the clock signal and that is coupled to the detector;
   an error detector that is coupled to the signal regenerator and to the signal generator, wherein the error detector compares a set of bits output from the signal generator to a corresponding set of bits output from the signal regenerator and determines the number of errors between the sets of bits output from the signal generator and the signal regenerator; and
   processing circuitry that is coupled to the error detector so as to compare the number of error to a threshold to determine a particulate concentration between the emitter and the detector.

2. The apparatus of claim 1, wherein the apparatus further comprises an amplifier that is coupled between the detector and the signal regenerator.

3. The apparatus of claim 2, wherein the apparatus further comprises a clock generator that is coupled to the signal generator and the signal regenerator.

4. The apparatus of claim 3, wherein the apparatus further comprises an intensity adjustment circuit that is coupled to the error detector and the driver, wherein the intensity adjustment circuit adjusts a drive current for the emitter.

5. The apparatus of claim 3, wherein the apparatus further comprises a pulse width modulator (PWM) that is coupled to the error detector and the driver, wherein the intensity adjustment circuit adjust the pulse width of a drive signal for the emitter.

6. The apparatus of claim 3, wherein the apparatus further comprises a bit length adjustment circuit that is coupled to the error detector.

7. The apparatus of claim 6, wherein the bit length adjustment circuit is coupled to the signal generator.

8. The apparatus of claim 3, wherein the apparatus further comprises a bit rate adjustment circuit that is coupled to the error detector and the signal generator.

9. The apparatus of claim 3, wherein the apparatus further comprises:
   an average value calculator that is coupled to the error detector; and
   a threshold adjustment circuit that is coupled to the average value calculator and the processing circuitry.

10. The apparatus of claim 3, wherein the apparatus further comprises:
    a carrier signal generator;
    a modulator that is coupled to carrier signal generator and that is coupled between the signal generator and the driver; and
    a demodulator that is coupled to the clock generator and the carrier signal generator and that is coupled between the amplifier and the error detector.

11. An apparatus comprising:
    a chamber;
    a signal generator that receives a clock signal;
    a driver that is coupled to the signal generator;
    an emitter that is coupled to the driver and that is secured to the chamber, wherein the emitter emits light;
    a detector that is adapted to receive light emitted from the emitter and that is secured to the chamber;

a signal regenerator that receive the clock signal and that is coupled to the detector;

an error detector that is coupled to the signal regenerator and to the signal generator, wherein the error detector compares a set of bits output from the signal generator to a corresponding set of bits output from the signal regenerator and determines the number of errors between the sets of bits output from the signal generator and the signal regenerator; and processing circuitry that is coupled to the error detector so as to compare the number of error to a threshold to determine a particulate concentration within the chamber between the emitter and the detector.

12. The apparatus of claim 11, wherein the apparatus further comprises an amplifier that is coupled between the detector and the signal regenerator.

13. The apparatus of claim 12, wherein the apparatus further comprises a clock generator that is coupled to the signal generator and the signal regenerator.

14. The apparatus of claim 13, wherein the apparatus further comprises an intensity adjustment circuit that is coupled to the error detector and the driver, wherein the intensity adjustment circuit adjusts a drive current for the emitter.

15. The apparatus of claim 13, wherein the apparatus further comprises a pulse width modulator (PWM) that is coupled to the error detector and the driver, wherein the intensity adjustment circuit adjust the pulse width of a drive signal for the emitter.

16. The apparatus of claim 13, wherein the apparatus further comprises a bit length adjustment circuit that is coupled to the error detector.

17. The apparatus of claim 16, wherein the bit length adjustment circuit is coupled to the signal generator.

18. The apparatus of claim 13, wherein the apparatus further comprises a bit rate adjustment circuit that is coupled to the error detector and the signal generator.

19. The apparatus of claim 13, wherein the apparatus further comprises:

an average value calculator that is coupled to the error detector; and a threshold adjustment circuit that is coupled to the average value calculator and the processing circuitry.

20. The apparatus of claim 13, wherein the apparatus further comprises:

a carrier signal generator;

a modulator that is coupled to carrier signal generator and that is coupled between the signal generator and the driver; and a demodulator that is coupled to the clock generator and the carrier signal generator and that is coupled between the amplifier and the error detector.

* * * * *